United States Patent
Arnott et al.

(10) Patent No.: US 7,710,566 B2
(45) Date of Patent: May 4, 2010

(54) METHOD AND APPARATUS FOR PHOTOACOUSTIC MEASUREMENTS

(75) Inventors: W. Patrick Arnott, Reno, NV (US); Hans Moosmuller, Reno, NV (US)

(73) Assignee: Board of Regents of the Nevada System of Higher Education on behalf of the Desert Research Institute, Reno, NV (US)

( * ) Notice: Subject to any disclaimer, the term of this patent is extended or adjusted under 35 U.S.C. 154(b) by 297 days.

(21) Appl. No.: 11/139,166

(22) Filed: May 27, 2005

(65) Prior Publication Data
US 2006/0290944 A1    Dec. 28, 2006

(51) Int. Cl.
*G01N 21/00*    (2006.01)
(52) U.S. Cl. .......... 356/432; 356/337; 356/480
(58) Field of Classification Search .......... 356/461, 356/480
See application file for complete search history.

(56) References Cited

U.S. PATENT DOCUMENTS

| | | | | |
|---|---|---|---|---|
| 5,024,526 | A * | 6/1991 | von Redwitz | 356/73 |
| 5,348,002 | A * | 9/1994 | Caro | 600/310 |
| 6,618,148 | B1 * | 9/2003 | Pilgrim et al. | 356/432 |
| 6,662,627 | B2 | 12/2003 | Arnott et al. | |
| 6,957,593 | B1 * | 10/2005 | Burns | 73/866 |
| 7,064,329 | B2 * | 6/2006 | Webber | 250/339.12 |
| 7,263,871 | B2 * | 9/2007 | Selker et al. | 73/24.02 |
| 2004/0094716 | A1 * | 5/2004 | Evan Webber | 250/339.12 |

OTHER PUBLICATIONS

"A Guide to Spectroradiometry: Instruments & Applications for the Ultraviolet," Bentham Instruments, Ltd., Reading, Berkshire UK (Jan. 1997).
Arnott, et al., "Towards Aerosol Light-adsorption Measurements with a 7-Wavelength Aethalometer: Evaluation with a Photoacoustic Instrument and 3-Wavelength Nephelometer," *Aerosol Science and Technology* 39: 17-29 (2005).
Arnott, et al., "Aerosol Light Absorption and Climate: Quantification by the Photoacoustic Methods," *Atmospheric Science Program Science Team Meeting* (Jan. 2005).
Arnott, et al, "Nitrogen Dioxide and Kerosene-Flame Soot Calibration of Photoacoustic Instruments for Measurement of Light Absorption by Aerosols," *Review of Scientific Instruments* 71(12) 4545-4552 (Dec. 2000).
Arnott, et al., "Photoacoustic Spectrometer for Measuring Light Absorption by Aerosol: Instrument Description," *Atmospheric Environment* 33: 2845-2852 (1999).
Gangl, et al., "Increase of Light Absorption of Carbon Particles by a Transparent Coating: Experimental Evidence," *Abstracts of the European Aerosol Conference* 2004 S439-S440 (2004).

(Continued)

*Primary Examiner*—Tarifur Chowdhury
*Assistant Examiner*—Tara S Pajoohi
(74) *Attorney, Agent, or Firm*—Ryan A. Heck; UNR-DRI Technology Transfer Office (57) ABSTRACT

Photoacoustic instruments and their methods of use are disclosed. Certain disclosed photoacoustic instruments include a resonator cavity, an acoustic detector, a laser, an optical power detector, and a scattering detector. Further disclosed photoacoustic instruments include a resonator cavity, an acoustic detector, an optical power detector, a plurality of laser beams, each laser beam having a different wavelength, and, optionally, a scattering detector.

15 Claims, 8 Drawing Sheets

OTHER PUBLICATIONS

Killinger, et al., "The Use of Photoacoustic Spectroscopy to Characterize and Monitor Soot in Combustion Processes," *Laser Probes for Combustion Chemistry* (1980).

Liu, et al., "Particle Size Distribution Retrieval from Multispectral Optical Depth: Influences of Particle Nonsphericity and Refractive Index," *Journal of Geophysical Research* 104(D24): 31,753-31,762 (1999).

Moosmüller, et al., "Cavity Ring-Down and Cavity_enhanced Dectection Techniques for the Measurement of Aerosol Extinction," *Aerosol Science and Technology* 39: 30-39 (2005).

Moosmüller, et al., "Time-resolved Characterization of Diesel Particulate Emissions. 2. Instruments for Elemental and Organic Carbon Measurements," *Environmental Science and Technology* 35: 1935-1942 (2001).

Moosmüller, et al., "Photoacoustic and Filter Measurements Related to Aerosol Light Absorption During the Northern Front Range Air Quality Study (Colorado 1996/1997)," *Journal of Geophysical Research* 103(D21): 28,149-28,157 (Nov. 20, 1998).

Moosmüller, et al., "Methods for Real Time, In Situ Measurement of Aerosol Light Absorption," *Air and Waste Management Association* 47: 157-166 (1997).

Schnaiter, et al., "UV-VIS-NIR Spectral Optical Properties of Soot and Soot-Containing Aerosols," *Journal of Aerosol Science* 34: 1421-1444 (2003).

Schurath, "The Effect of Coatings on the Optical Properties of Aerosol Particles" (May 16, 2003).

Sheridan, et al., "The Reno Aerosol Optics Study: An Evaluation of Aerosol Absorption Measurement Methods," *Aerosol Science and Technology* 39: 1-16 (2005).

Varma, et al., "Toward an Ideal Integrating Nephelometer," *Optics Letters* 28(12): 1007-1009 (Jun. 15, 2003).

Virkkula, et al., "Modification, Calibration and a Field Test of an Instrument for Measuring Light Absorption by Particles," *Aerosol Science and Technology* 39: 68-83 (2005).

* cited by examiner

METHOD AND APPARATUS FOR PHOTOACOUSTIC MEASUREMENTS

STATEMENT OF GOVERNMENT SUPPORT

This invention was made with United States Government support under NSF MRI account Grant No. ATM-0216572. The United States Government has certain rights in the invention.

FIELD

Photoacoustic instruments and their methods of use are disclosed. More specifically, the disclosure relates to photoacoustic instruments that include a scattering detector or are capable of making measurements at a plurality of wavelengths.

BACKGROUND

Air pollution and anthropogenic aerosol are typical byproducts of combustion, such as from automobiles, power plants, factories, fire places, and the like. Incomplete combustion often produces an aerosol that strongly absorbs visible light and has significant elemental carbon content. Not only do these aerosols negatively impact visibility, they may be a health hazard when inhaled and may alter the global radiation balance and general circulation. Common windborn dust from deserts also absorbs light at UV wavelengths.

A number of techniques have been devised to measure light absorption by aerosols. Many techniques capture aerosols on filters, followed by an optical measurement to determine aerosol light absorption. The Aethalometer is a real time version of such an instrument. However, the use of filters may alter particles in the aerosol and therefore the data obtained from such instruments may not accurately represent the natural state of the aerosol. Accordingly, these techniques may produce data which does not accurately describe the aerosol.

Photoacoustic techniques have also been used to measure the properties of aerosols. In the photoacoustic technique, electromagnetic energy is applied to a sample, some of which is absorbed by the aerosol and converted to heat. Because the particles in the aerosol are small, and have sufficiently high thermal conductivity, the absorbed heat will flow rapidly to the surrounding air. When heated, the air expands its volume or pressure. By placing the aerosol laden air into an acoustic resonator and modulating electromagnetic power at the resonance frequency of the acoustic resonator, the varying pressure disturbance (acoustic signal) can be amplified by the buildup of a standing acoustic wave in the resonator. Thus, by measuring the sound pressure associated with aerosol light absorption, a measure of elemental carbon concentration can be obtained.

Typical photoacoustic instruments measure light absorption. However, it is often necessary to measure extinction, which is the sum of absorption and scattering due to interaction of the particles with the electromagnetic radiation, to obtain more information on the climate impact of aerosols. One method of measuring extinction uses a laser as the light source and measures optical power before and after the introduction of an aerosol sample. The noise floor of such a measurement, however, can be very large ($10^3$ $Mm^{-1}$) while the noise floor of the scattering and absorption measurements are less than 1 $Mm^{-1}$ for comparable measurement times. Although cavity-ringdown extinction measurements have been combined with scattering measurements, these methods are still inadequate for many applications that require light absorption measurements.

For example, wood smoke from smoldering fires can have a single scattering albedo (ratio of scattering and extinction) of 0.99, so the extinction and scattering measurements must be unrealistically accurate and precise to obtain absorption by subtraction. Extinction measurements are generally plagued by imperfections in the amount of forward-scattered light reaching the detector in excess of the on-axis light, and scattering measurements may suffer from angular truncation errors.

For example, a readily available scientific nephelometer, manufactured by TSI, records particle scattering from 7 degrees in the forward direction to approximately 173 degrees in the backward direction. Scattering from submicron particles can be corrected by use of the Angström coefficient; however, such an approach for super-micron particles can produce large errors as described in Anderson, T. L. and J. A. Ogren (1998). "Determining Aerosol Radiative Properties Using the TSI 3563 Integrating Nephelometer" *Aerosol Science and Technology* 29(1): 57-69.

Another limitation of many photoacoustic instruments is that they are only capable of monitoring one wavelength at a time. As a result, prior techniques often require multiple instruments, or multiple sequential experiments with one instrument, in order to obtain information about multiple aerosol components or characteristic of an aerosol component. For example, more than one measurement may be needed to determine both the amount of particulate matter in an aerosol and to get information on the aerosol's composition, such as coatings on the particles.

SUMMARY

The present invention provides photoacoustic instruments and their methods of use. Certain embodiments provide a photoacoustic instrument that allows for simultaneous measurement of scattering and absorption. In certain embodiments, the instrument includes a laser, a resonator cavity, an acoustic detector, an optical power detector, and a scattering detector. In operation, the laser is passed through a sample. The particles of the sample absorb some of the laser energy, which can be detected by the optical power detector. The sample also scatters some of the laser energy, which may be detected by the scattering detector. In certain embodiments, because the scattering and absorption coefficients of the sample are known, its extinction can be calculated as a simple sum of these coefficients.

Further embodiments provide a photoacoustic instrument that allows for simultaneous measurement of absorption and, in some implementations, scattering, at multiple wavelengths. In certain embodiments, the instrument includes a plurality of laser beams having different wavelengths, a resonator cavity, an optical power detector, an acoustic detector, and, optionally, a scattering detector. The power modulation frequencies of the laser may be selected so that they fall within the passband of the acoustical resonator.

Further embodiments provide methods of using the disclosed photoacoustic instruments. For example, certain disclosed photoacoustic instruments can be used to gain chemical or structural information about the components of an aerosol. Certain methods allow for trace gases to be detected in addition to aerosol. Further examples provide methods of calibrating a photoacoustic instrument. Certain disclosed photoacoustic instruments can be carried on an aircraft, such as for plume detection. In further applications, the photoacoustic instruments disclosed herein can be used for environmental monitoring, such as for pollution monitoring. In a particular example, a disclosed photoacoustic instrument is used to detect a light absorbing aerosol or components thereof, such as black carbon and windborn dust.

There are additional features and advantages of the present invention or varying embodiments of the present invention. They will become apparent as this specification proceeds.

In this regard, it is to be understood that this is a brief summary of varying aspects of the present invention or various embodiments or alternative embodiments of the present invention. The present invention therefore need not provide all features noted above nor solve all problems or address all issues in the prior art noted above.

DETAILED DESCRIPTION

Unless otherwise explained, all technical and scientific terms used herein have the same meaning as commonly understood by one of ordinary skill in the art to which this invention belongs. In the case of conflict, terms have the meanings provided in the present disclosure.

The singular terms "a," "an," and "the" include plural referents unless context clearly indicates otherwise. Similarly, the word "or" is intended to include "and" unless the context clearly indicates otherwise. The term "comprises" means "includes."

General Components of a Photoacoustic Instrument

Figure 1:
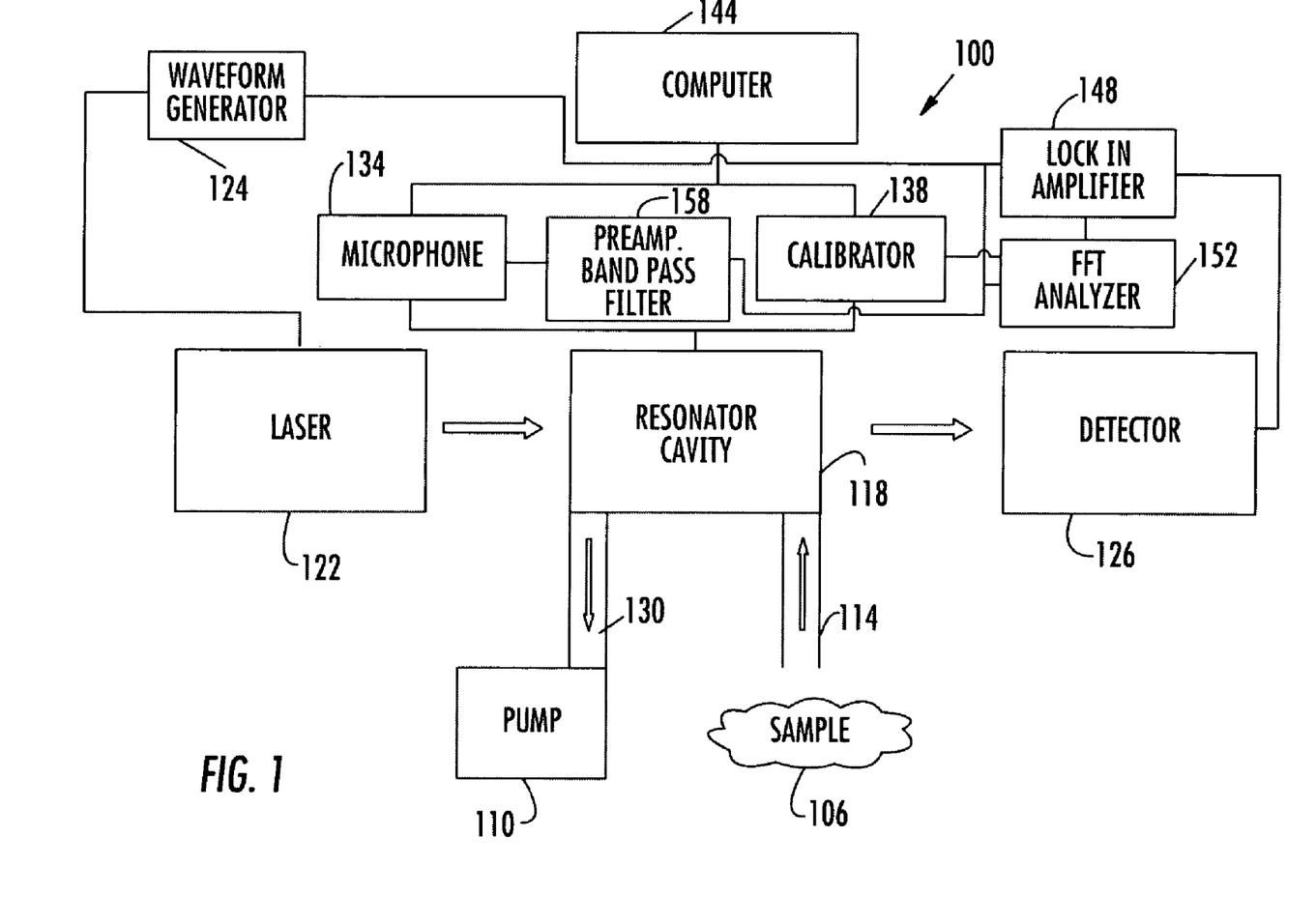
FIG. 1 is a block diagram of a photoacoustic instrument.

FIG. 1 is a block diagram of a photoacoustic spectrometer 100 for measuring the properties of an aerosol sample 106. A pump 110 pulls a portion of the sample 106 through a sample inlet 114 into a resonator 118. While in the resonator 118, the sample 106 is irradiated with a laser beam generated by a laser 122. In operation, the laser power is modulated at the acoustic resonance frequency using the square wave output of a waveform generator 124. After interacting with the sample, radiation from the laser beam enters an optical power detector 126. The sample 106 is removed from the resonator 118 through a sample outlet 130.

After absorbing energy from the laser beam, the heated particles in the sample 106 transfer their heat to the surrounding air, generating an acoustic signal that is detected by an acoustic sensor 134, such as a microphone. In order to calibrate the instrument 100, a calibrator 138, such as a piezoelectric transducer, may be used to produce a known acoustic signal. Of course, other acoustic sources may be used to calibrate the spectrometer 200, if desired. A computer 144 is in communication with the laser 122, the detector 126, the microphone 134, and the calibrator 138 and may be used to determine the absorption of the sample.

In addition to modulating the laser power, the waveform generator 124 provides timing for phase-sensitive detection of the signal produced by the microphone 134 by a lock-in amplifier 148 or a Fast Fourier Transform (FFT) analyzer 152. The signal produced by the microphone 134 may be amplified with a low noise pre-amplifier 158 (for example, by a factor of 200) and filtered using a bandpass filter 158 (for example, a bandpass filter with a 1 kHz bandwidth centered at 1500 Hz). Pre-amplification helps provide an adequate signal level for the FFT analyzer 152. The FFT analyzer 152 determines the magnitude of the Fourier component of acoustic pressure ($P_m$) at frequency $f_o$, the resonance frequency of the resonator cavity 118. The FFT analyzer 152 also can be used to calibrate the resonator 118 by issuing a single cycle of a sine wave, or a swept sine wave, to the calibrator 138. In response, the calibrator 138 produces a known acoustic signal that is used to calibrate the microphone 134.

Therefore, the resonator 118 may be calibrated by obtaining the ratio (transfer function) of the microphone response to the acoustic drive signal. The computer 144 receives the transfer function, and fits it to a standard resonance response function as a function of Q (the resonator quality factor), $f_o$, and the peak of the transfer function. The lock-in amplifier 148 can be used to determine the phase of the signal of the microphone 134 relative to the timing signal generated by the waveform generator 124, and to determine the response of the detector 126 at $f_o$, but may be omitted, if desired. The FFT analyzer 152 can also perform this function. The detector may be calibrated with a laser power meter (not shown). The noise floor of the measurement can be determined, at the same time as the signal, from the weighted average of the electrical signal within the resonance response curve, excluding the signal exactly at the modulation frequency (resonance frequency of the resonator 118).

The programmable preamplifier 158 may be used to amplify acoustic signals. High pass and low pass filters with settings of 24 dB per octave roll off may be used on the preamplifier 158.

The entire measurement procedure may be automated using the computer 144. The preamplifier 158 and other components of the instrument 100 may be connected to the computer 144 by any suitable method, including a serial port, IEEE 488 connection, or direct digital control. National Instruments Lab View software may be used to interface the computer 144 with the instrument 100. The instrument may be calibrated before, during, or after an experiment. In certain examples, the calibration procedure lasts for about 5 seconds. For example, each measurement of light absorption may be preceded with a resonator calibration using the FFT analyzer 152. In at least certain implementations, the signal-to-noise ratio is proportional to the square root of the FFT analyzer 152 total time of averaging, and directly proportional to power of the laser 122.

The computer 144 uses an algorithm to process the electrical signal. The algorithm calculates light absorption, which is proportional to the mass concentration of light absorbing particles in the sample. The light absorption may be calculated from the formula below using the acoustic pressure measured with the microphone 134, the resonator quality factor, the resonant frequency, the Fourier component of the laser beam power, and the cross sectional area of the resonator 118.

$$B_{abs} = P_m \frac{1}{P_L} \frac{A_{res}}{\gamma - 1} \frac{\pi^2 f_0}{Q}$$

In the formula above, $B_{abs}$ is the absorption in dimensions of inverse distance; $P_m$ is the acoustic pressure measure by the microphone 134; $P_L$ is the Fourier component of laser beam power at $f_o$; $f_0$ is the resonance frequency; $A_{res}$ is the resonator cross sectional area; gamma is the ratio of isobaric and isochoric specific heats; and Q is the resonator quality factor.

Photoacoustic Instrument Incorporating a Scattering Detector

Figure 2:
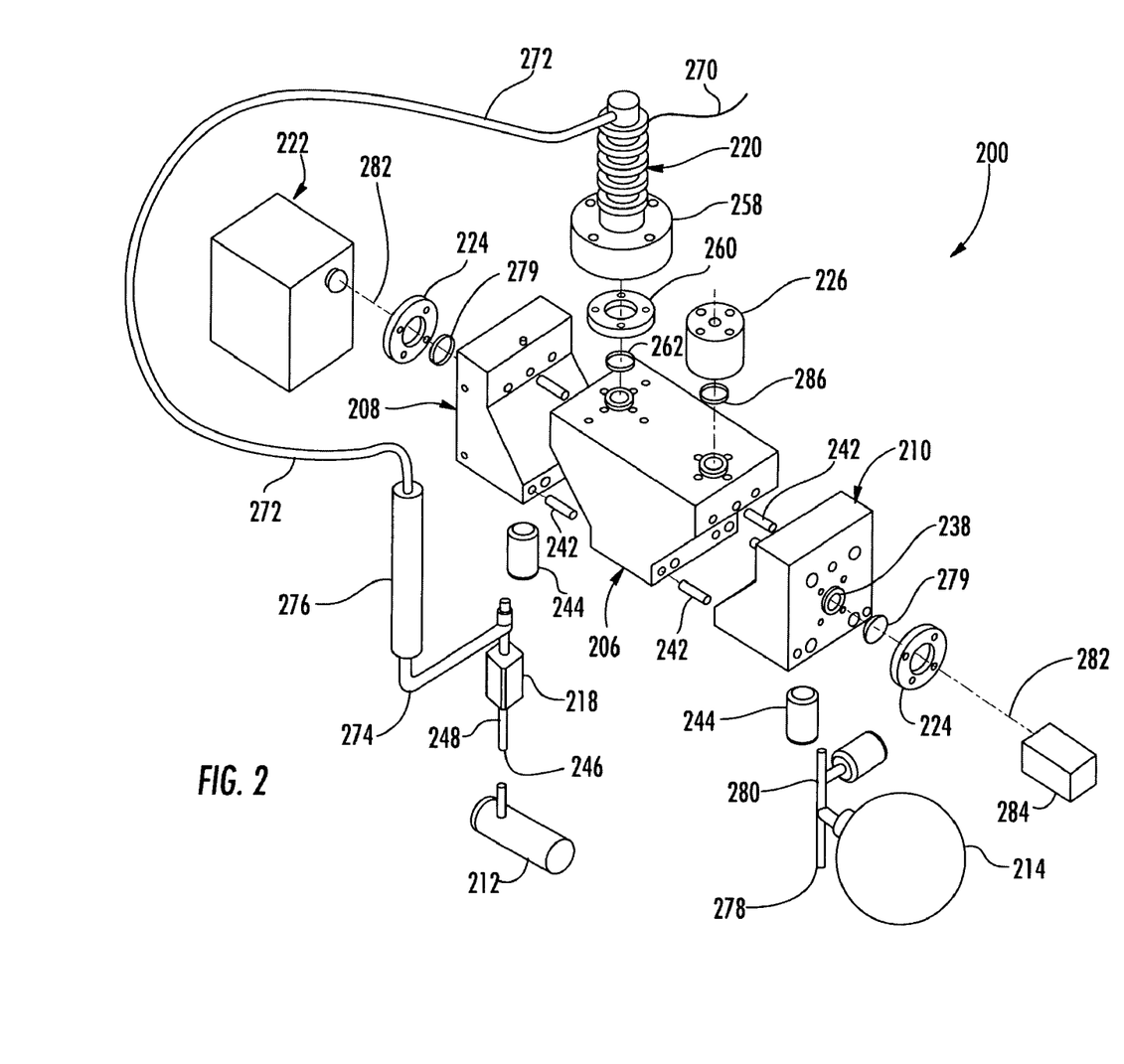
FIG. 2 is a schematic diagram illustrating a photoacoustic instrument.
Figure 3:
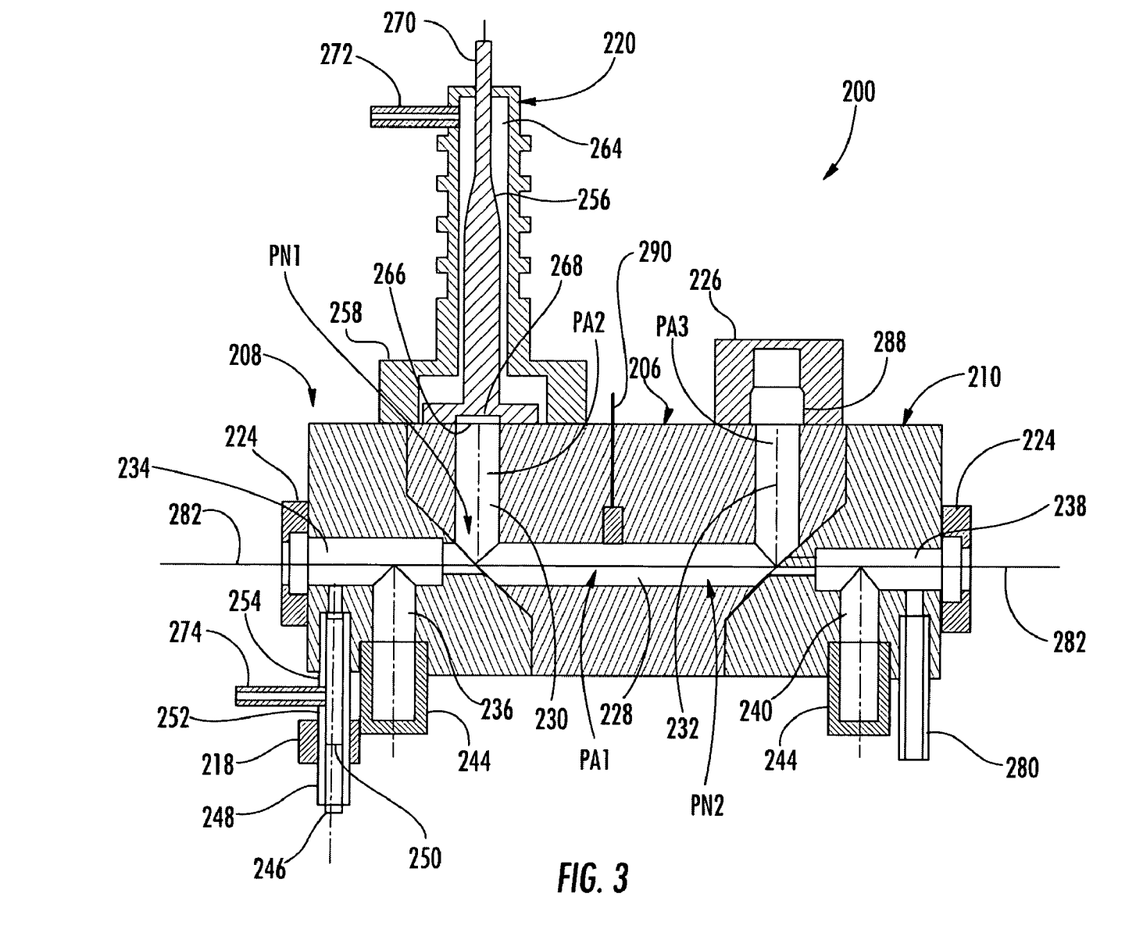
FIG. 3 is an additional schematic diagram illustrating the photoacoustic instrument of FIG. 2, which includes a scattering detector.

FIGS. 2 and 3 provide a more detailed view of a photoacoustic instrument 200. Additional features which may be included in the photoacoustic instrument 200 can be found in U.S. Pat. No. 6,662,627, hereby incorporated by reference in its entirety.

The instrument 200 includes a resonator 206, left 208 and right 210 coupling sections, a pump 212, a low frequency acoustic bandstop filter 214, a high frequency acoustic bandstop filter 216, a flow sonic orifice 218, a microphone assembly 220, a laser 222, windows 224, and a piezoelectric calibrator 226.

A resonator cavity 228 (FIG. 3) is formed in the resonator 206. A microphone bore 230 intersects the resonator cavity 228 perpendicularly to the resonator cavity 228. A calibrator bore 232 also perpendicularly intersects the resonator cavity 228. Bores 230 and 232 are located at pressure nodes PN1 and PN2. The pressure nodes allow the bores 230, 232 to have a minimal effect on the acoustics of the resonator cavity 228. If desired, the cavity may be coated with a highly reflecting coating, such as a near-Lambertian barium sulfate coating for the purpose of assisting with the integration of scattered light.

A bore 234 passes through the left coupling section 208 and a de-tuning bore 236 perpendicularly intersects bore 234. Similarly, a bore 238 passes through the right coupling section 210 and a de-tuning bore 240 perpendicularly intersects bore 238. Left and right coupling sections 208, 210 are attached to the resonator 206 using alignment pins 242. One half of each alignment pin 242 rests in an aperture in its respective coupling section 208, 210, and the other half rests in an aperture in the resonator 206. The coupling sections 208, 210 are affixed to the resonator 206 by bolts or other fasteners or fastening material (not shown).

The resonator 206 and coupling sections 208, 210 are preferably formed out of aluminum. For example, a block of aluminum can be milled and bored to form the resonator 206 and coupling sections 208, 210. Other metals and manufacturing techniques could also be used. For example, several tubes could be joined together to form the resonator 206 and coupling sections 208, 210.

De-tuning cavities 244 are attached to de-tuning bores 236 and 232. The de-tuning cavities 244 serve to reduce the coupling of acoustic noise into the resonator cavity 228 at its acoustic resonance frequency, and are particularly useful for decoupling the resonator from light absorption by the windows or deposits on the windows.

A pump 212 (FIG. 2) is attached to an air outlet 246. An outlet pipe 248 connects pump 212 to a flow sonic orifice 218. Flow sonic orifice 218 includes a disc 252 mounted in the path of airflow. A hole 250 is formed in the disc 252. The speed of air flowing through the flow sonic orifice 218 approaches the speed of sound in the gas. The orifice 218 is deemed operational when the pump pressure is sufficient to make the flow rate approach the speed of sound. Sound from the pump 212 that would normally travel into the resonator 206 is reflected at the flow sonic orifice 218 back toward the pump 212, thereby preventing the sound from interfering with measurements in resonator cavity 228. A suitable flow sonic orifice 218 is commercially available from Okeefe Controls. The flow sonic orifice 218 is attached to bore 234 by pipe 254.

An equalizer tube 272 is connected above the flow sonic orifice 218 by an equalizer pipe 274. Equalizer tube 272 is connected to the microphone cavity 264. A microphone assembly 220 is mounted to a resonator 206. The microphone assembly 220 includes a microphone 256 contained in a microphone enclosure 258. Enclosure 258 is attached by a microphone mount 260 to resonator 206. A seal 262 seals the microphone 256.

The microphone 256 comprises a microphone cavity 264, a flexible, electrically conducting, membrane 266 that faces into bore 230, and a fixed metallic back plate 268. Membrane 266 and back plate 268 form a parallel plate capacitor. Accordingly, acoustical signals produced by the resonator 206 force the movable membrane 266 to change position with respect to the back plate 268, thereby changing the capacitance. A wire 270 provides an electrical signal from the microphone 220. A suitable microphone assembly 220 is commercially available from ACO Pacific.

When a continuous air sample is pulled through the resonator 206, the static pressure on the movable membrane 266 could be different from that on the back plate 268, causing a drift of the microphone calibration and false measurements. The equalization tube 272 and pipe 274 prevent this pressure change and accompanying calibration drift. The equalization tube 272 may contain a drying agent (not shown), such as Dryerite (Cole-Palmer) in a drying section 276. The drying agent removes water vapor in the air. The water vapor could condense between the back plate 268 and movable membrane 266 of the microphone 256, causing it to short out, or the water vapor could condense on the preamplifier electronics in the microphone 256, causing them to fail.

An air sample inlet 278 admits sample air into the resonator 206. Inlet 278 is at the end of inlet pipe 280. Inlet pipe 280 is connected to bore 238. A low frequency acoustic band stop filter, or resonator, 214 and a high frequency filter 216 are attached to inlet pipe 280. Low frequency filter 214 may be a Helmholtz resonator. A Helmholtz resonator is an enclosed volume, such as a metal sphere with a tube extending from the sphere to the inlet pipe. Helmholtz resonators reflect sound of certain wavelengths, the reflected wavelengths depending upon the dimensions of the resonator. Helmholtz resonator 214 rejects frequencies well below the resonant frequency of the acoustic resonator cavity 228. Filter 214 rejects unwanted noise from outside the instrument 200 that enters through the inlet 278. Similarly, filter 216 rejects higher frequency noise from outside the instrument 200.

In certain embodiments, the low frequency filter 216 may be an acoustic notch filter. An acoustic notice filter may be constructed using tubes of the same length as the resonator cavity 228 (i.e. the acoustic wavelength), and operate by destructive interference. The acoustic notch filters provide an open volume so that the volumetric efficiency of undesired sound generated by light absorption on windows 224, or in the acoustic notch filter itself, is quite low. The acoustic notch filter blocks most of the noise from the pump 212 and spurious sound produced by absorption of light on the windows 224 from entering the instrument 200.

A laser 222 is aligned with windows 224. A seal 279 seals window 224 to the coupling sections 208, 210. Laser 222 generates a laser beam 282. Suitable lasers include a 532 nm Nd:YAG laser diode pumped laser with a modulated power output of about 60 mW. A 685 nM laser diode with a modulated power output of about 87 mW may also be used. Other wavelengths may be used, as desired, such as a 1047 nm, 676 nm, or 870 nm lasers. Suitable lasers are available from Crystalaser.

Light having a wavelength of 1047 nm wavelength is particularly useful for measuring the photoacoustic signal from black carbon, as 1047 nm lasers can be obtained with very high power. In addition, black carbon has an acceptably strong absorption at this wavelength. In one example, rather than adding this wavelength directly and including it in the modulation, the system may be time sliced to measure at other wavelengths, such as one or more nominally visible wavelengths, and then at 1047 nm.

Laser beam 282 passes through window 224, bore 234, and into resonator cavity 228, where it irradiates the sample. The laser beam 282 then passes through bore 238 and window 224. Photodetector 284 receives the laser beam 282 at this end of the resonator 206.

A piezoelectric calibrator 226 is mounted to resonator 206 above calibrator bore 232. A seal 286 is used to seal calibrator 226 to the resonator 206. The piezoelectric calibrator 226 has a piezoelectric element 288 adjacent bore 232. The piezoelectric calibrator element 288 is commercially available from RadioShack, for example. The piezoelectric element 288 is turned on in an alternating fashion between measurements. The piezoelectric element 288 sends a known acoustic signal into the resonator 206 in order to obtain acoustic calibration of the resonator cavity 228 (resonance frequency and quality factor). Other calibration sources, such as a speaker, can be used to generate a known acoustic signal Certain embodiments of the photoacoustic instrument 200 include a detector 290 to detect laser light scattered by particles in the sample aerosol. In certain embodiments, the detector 290 is a cosine-detector, such as an integrating reciprocal nephelometer which measures the total scattering cross section. Suitable cosine detectors can be manufactured with a flat circular surface of Teflon or Spectralon (Spectralon is a registered trademark of, and is available from Labsphere, Inc. of North Sutton, N.H.), and a photomultiplier tube to detect light entering the cosine detector. Another suitable nephelometer is described in Varma et al. (2003). "Toward an ideal integrating nephelometer." *Optics Letters* 28(12): 1007-1009, which is hereby expressly incorporated by reference in its entirety.

The detector 290 may use a cosine-weighted sensor head 292 for aerosol scattering measurements. The sensor head 292 uses an optical fiber (not shown) coupled to a Teflon cosine diffuser (not shown, available from Bentham Instruments, Reading, UK). The detector 290 may include a photomultiplier tube (PMT), photodiode, or CCD to measure light scattered by the particles in a sample. Phase sensitive detection is used to detect the optical power of light scattered by particles, just as is done with the light absorption signal. Scattering and absorption sensors operate concurrently, as this is can be important for plume detection or detection of other short-lived events.

As used herein, "cosine-weighted" refers to the weighting of light power received at the detector 290 as a function of the light scattering angle with respect to the normal to the sensor. Light scattered by aerosols in the middle of the resonator cavity 228 occurs at an angle of 90 degrees to the laser beam direction, and this scattering receives a 'weighting' of unity. Light scattered at other angles is 'weighted' by the cosine of the angle relative to the normal of the sensor, e.g., by the sine of the scattering angle. This weighting of the light power scattered by aerosols ensures that the measured signal, such as with the PMT, is proportional to the total aerosol scattering cross section. Because embodiments of the instrument 200 which include scattering detector 290 allow for simultaneous measurement of scattering, absorption, and albedo, they can provide more accurate calculation of extinction and can determine these components. In certain implementations, the instrument 200 calculates extinction with a truncation angle of less than 5 degrees. In other implementations, such as where the resonator is coated with barium sulfate (or a similar coating), the resonator and cosine sensor comprise an integrating nephelometer with a truncation angle of 1 degree.

Resonator Characteristics

The resonator cavity 228 is a full wavelength resonator with pressure nodes PN1 and PN2 at the ends of the resonator cavity 228 and a pressure antinode PA1 at the center (A pressure node is a region of very low acoustic pressure. A pressure antinode is a region of highest acoustic pressure in the acoustic standing wave in the resonator cavity 228.). Where the coupling sections 208, 210 join the resonator 206, the mating surfaces are angled or sloped at 45 degrees to accommodate insertion of the laser beam 282. The pressure nodes PN1 and PN2 are located where the laser beam 282 enters the resonator cavity 228. The diameter of the bores 234, 238 is much smaller than the acoustic wavelength and, along with being located at the pressure nodes, allows the bores 234, 238 to have a minimal effect on the acoustics of the resonator 206.

The laser beam 282 is modulated at the acoustic resonance frequency of the resonator 206 so that sound produced by light absorption is amplified by the resonator cavity 228. This arrangement also helps to reduce the coupling of noise into the resonator 206 at the acoustic frequency since holes are located at the pressure nodes. In order to maximize sensitivity, the microphone element 266 is located at a pressure antinode PA2 at the end of microphone bore 230. Similarly, the piezoelectric calibrator 226 is located at a pressure antinode PA3 at the end of calibrator bore 232.

Method of Operating a Photoacoustic Instrument

Figure 4:
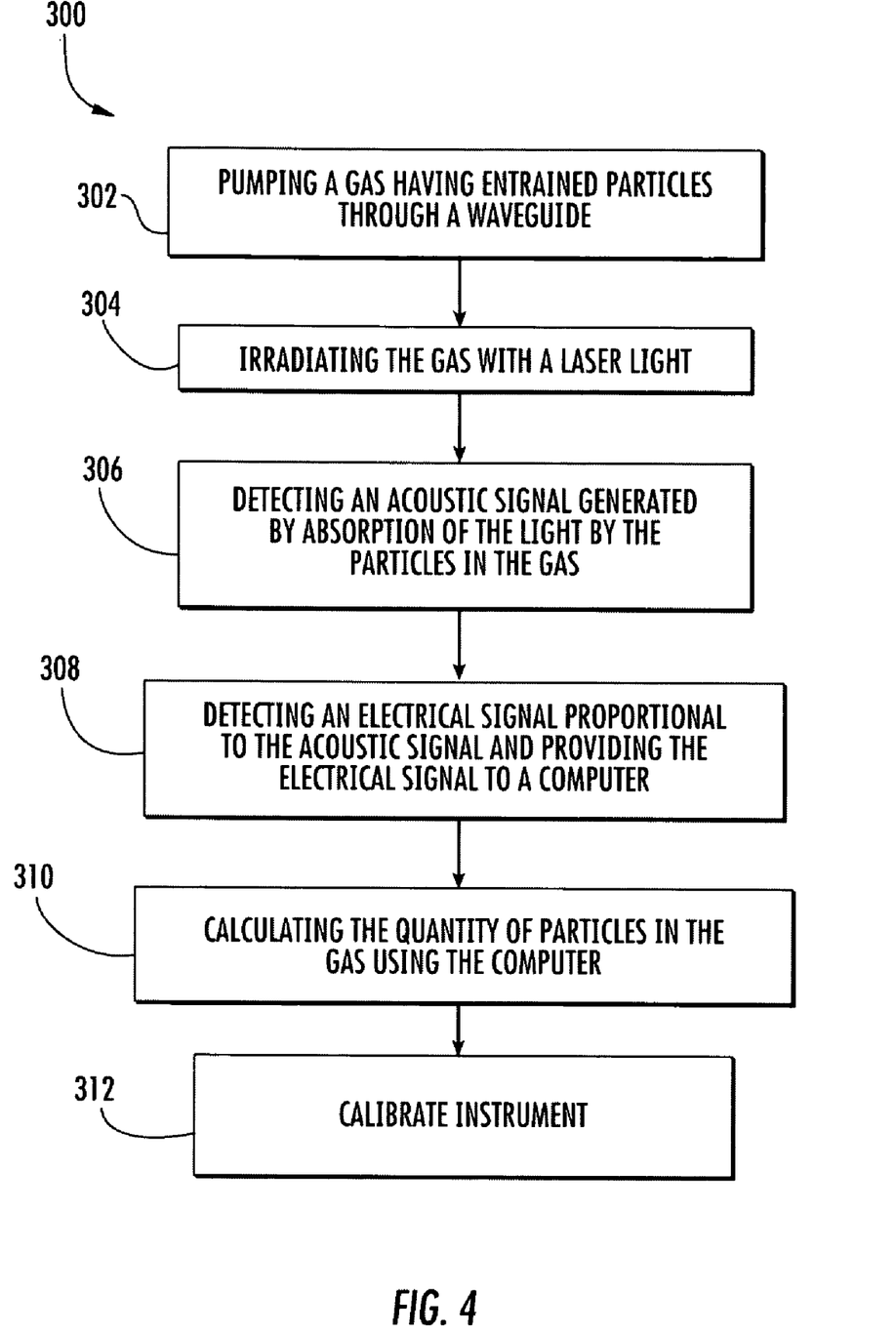
FIG. 4 is a flow chart of a method of operating a photoacoustic instrument.

Referring to FIG. 4, a flowchart 300 of a method of operating a photoacoustic instrument, such as photoacoustic instrument 200, is shown. First, at step 302, sample gas, such as an aerosol containing black carbon particles, is continuously pulled through the resonator cavity 228 by pump 212. The air flows into inlet 278 and is expelled from the pump 212.

Next, at step 304, the laser beam 282 passes through window 224, through bore 234, resonator cavity 228, bore 238, window 224, and is received by photodetector 284. The laser beam power amplitude and phase at the modulation frequency are obtained from photodetector 284. The modulation frequency is the resonance frequency of the acoustic resonator 206.

As the sample is irradiated with the laser beam 282, the heat from light absorption transfers from particles in the sample to the surrounding air and an acoustic pressure wave or sound wave is generated. The sound is generated near the center of resonator waveguide cavity 208 in the region of the pressure antinode PA1. The radiation absorbed by particles in the sample results in pressure variations in a given volume. The pressure variation is proportional to the amount of energy absorbed.

The pressure wave is detected by microphone 256 at step 306. The magnitude of the wave is proportional to the amount of light absorption and the laser power. If the particles are sufficiently small, the concentration of particles can be determined from the amount of light absorbed.

At step 308, the microphone 256 generates an electrical signal, which, at least for samples with sufficiently small particles, is proportional to the mass concentration of particles in the sample. The electrical signal is provided to an amplifier (FIG. 1, amplifier 158) and computer 144 (FIG. 1) through wire 270. At step 310, the computer 144 calculates the concentration of the particles as well as the amount of light that is being absorbed or blocked by the particles.

At step 312, calibration is performed between light absorption measurements. The piezoelectric element 286 generates a known acoustic signal to calibrate the sensor.

Selection of Laser Wavelengths

The waveform generator 124 (FIG. 1) can be used to modulate the laser power at the spectrometer acoustic resonance frequency. The wavelength is preferably selected to avoid gaseous atmospheric light absorption, though it may also be chosen to explicitly measure light absorption by gases as well. If a gaseous absorption is due to a gas with constant atmospheric concentration (e.g., $O_2$), a background signal is acceptable. This background signal is only constant if the convolution of laser and gas spectrum is constant. The situation is worse if the concentration of the absorbing gas varies with time (e.g., $H_2O$, $NO_2$, $O_3$, etc.). Atmospheric absorption coefficients $B_{absg}$ have been calculated for the 1976 US Standard Atmosphere (NASA, 1976) at sea level (T=288 K, p=1013 mB, RH=46%) with a recent version (FASCOD3) of the Fast Atmospheric Signature Code (FASCODE) (Clough et al., 1981; Chetwynd et al., 1994) and can be used to select a wavelength with little gaseous absorption.

Figure 5:
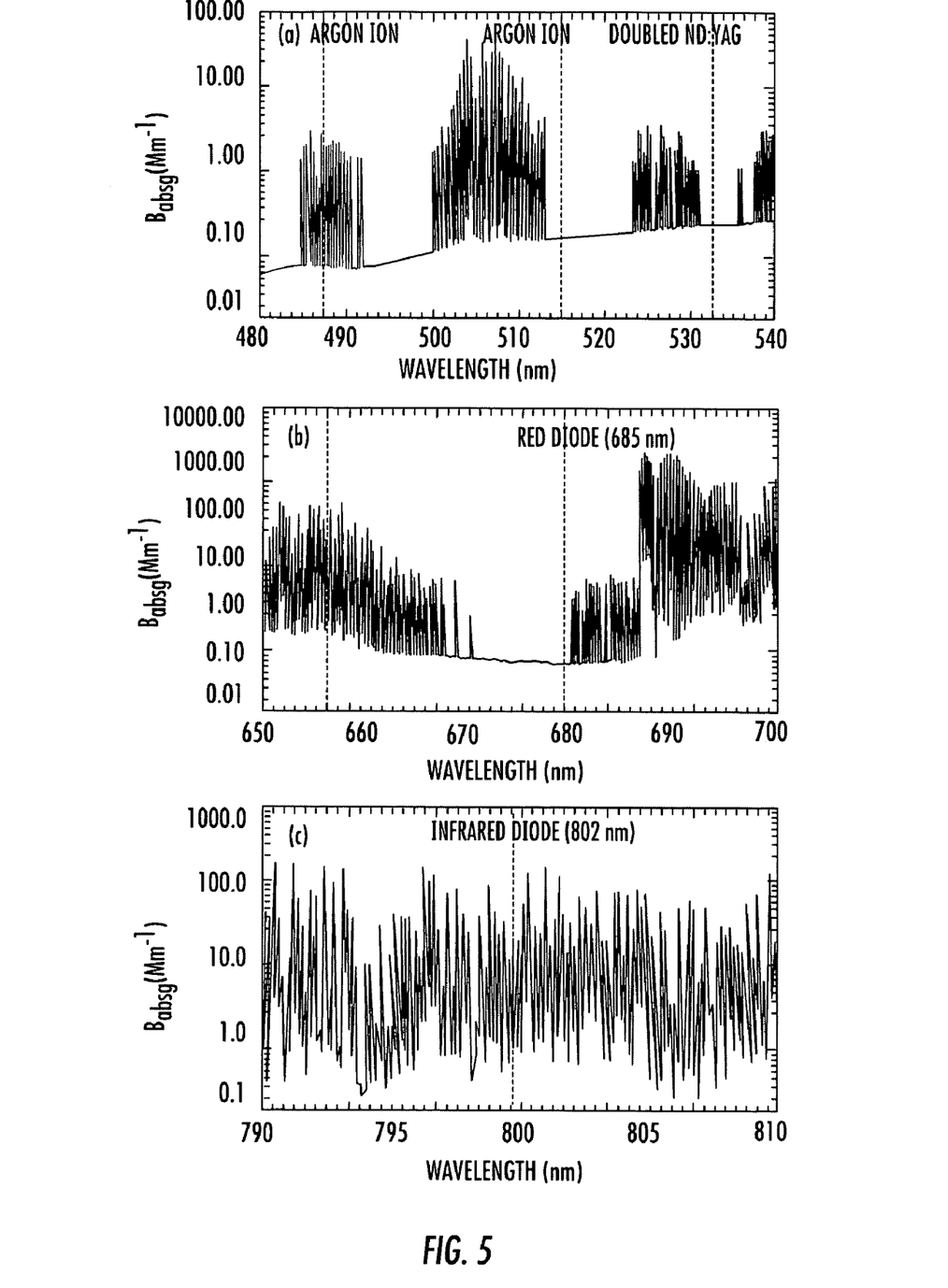
FIG. 5 is a graph showing the FASCODE atmospheric absorption spectra in the (a) blue-green, (b) red, and (c) near infrared regions.

Three spectral regions of interest are shown in FIG. 5. The blue-green region (FIG. 5a) contains three laser lines of interest: the argon ion laser lines at 488.0 and 514.5 nm; and the frequency doubled Nd:YAG laser line at 532.0 nm. The gaseous absorption coefficient is less than 0.1 $Mm^{-1}$ for both argon laser lines and less than 0.2 $Mm^{-1}$ for the Nd:YAG laser line.

The red spectral region shown in FIG. 5b includes a red diode laser wavelength of 685 nm, and the near infrared spectral region shown in FIG. 5c contains Petzold's and Niessner's diode laser wavelength of 802 nm. The absorption coefficient for a diode laser line cannot be specified as easily as for narrow band fixed frequency lasers. The diode laser center wavelength is a function of operating temperature (tuning coefficient of about 0.3 nm $K^{-1}$). High power diode lasers have typical bandwidths of 2 nm, as can be measured with an optical spectrometer. However, the order of magnitude of the respective gaseous absorption may be estimated by averaging the calculated absorption coefficients over a 2 nm interval centered on the nominal laser wavelength. This results in a gaseous absorption coefficient of about 0.1 $Mm^{-1}$ for the 685 nm laser diode and about 8 $Mm^{-1}$ for Petzold's and Niessner's diode laser (802 nm). FIG. 5b also indicates that the 671-680 nm region is well suited for diode-laser-based measurement of aerosol light absorption with a gaseous continuum absorption coefficient around 0.1 M $m^{-1}$ and no individual absorption lines.

It should be kept in mind that these conclusions are only valid for the specified atmospheric composition. Especially high concentrations of ambient ozone ($O_3$) and nitrogen dioxide ($NO_2$) can increase gaseous absorption in the blue-green spectral region, while water vapor can have a similar effect in the red and near infrared region. Gas denuders can be used to remove certain interfering trace gases, such as $NO_2$ and $O_3$.

Figure 6:
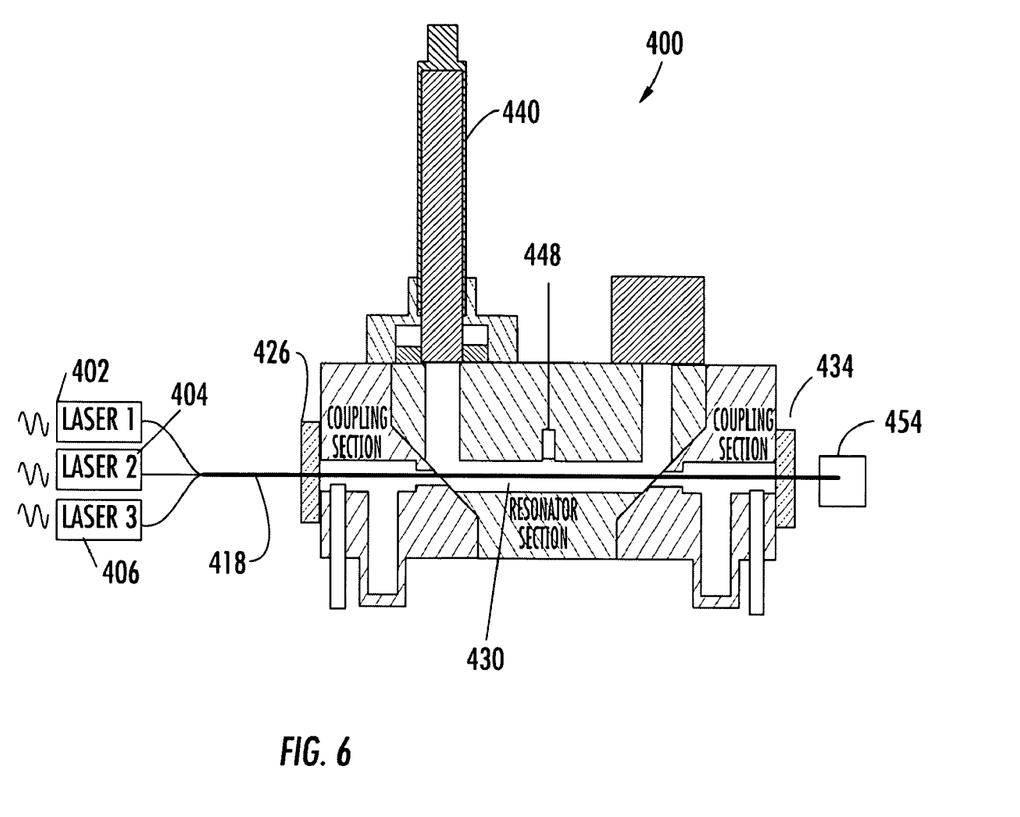
FIG. 6 is a schematic diagram of a photoacoustic instrument capable of simultaneously measuring absorption at multiple wavelengths.

Photoacoustic Instrument Capable of Measuring Absorbance at Multiple Wavelengths FIG. 6 illustrates a photoacoustic spectrometer 400 that can obtain data at a plurality of wavelengths. The spectrometer 400 is constructed substantially as described in FIGS. 2 and 3. However, the scattering detector is optional. As shown, the spectrometer 400 has three laser beams having three different wavelengths. However, more or less laser beams could be used.

As shown in FIG. 6, in a photoacoustic instrument 400 the output from lasers 402, 404, 406 are combined into a collimation fiber 418. Each laser beam may have its power modulated at different frequencies. Each laser is modulated at a different frequency within the passband of the acoustical resonator so that simultaneous detection at all wavelengths is possible. The lasers can also be operated in series.

The laser beam from the collimation fiber 418 is passed though an input coupler 426 and into a resonator cavity 430. After passing through a sample in the resonator cavity 430, the laser beam exits the resonator cavity 430 through an output coupler 434. The input coupler 426 and the output coupler 434 could also constitute a multipass mirror system, which allows the combined laser beam to make numerous passes through the resonator cavity 430 for enhanced sensitivity. Multispectral measurements are obtained by separating the three modulation frequencies from the time domain signals obtained at the microphone 440, optical power detector 454, and, optionally, at a scattering detector 448. When scattering detector 448 is used, it is preferably capable of measure scattering at a plurality of wavelengths.

Although FIG. 6 illustrates a photoacoustic spectrometer using a single collimation beam 418, other laser setups could be used. For example, a plurality of lasers could be placed proximate one another such that they are collinear or are close to one another. In addition, fewer lasers may be used than the number of beams produced. For example, a single laser may be used to produce multiple beams, such as through use of a diffraction grating.

Applications:

The ability to measure scattering and absorption allows information to be obtained about the materials present in an aerosol sample. Scattering information provides information about the size of the particles in an aerosol sample. For example, when air samples are being measured to determine black carbon content, an absorption wavelength dependence of $\lambda^{-1}$ indicates that the sample mostly contains black carbon. Very large particles cause the scattering to exhibit no wavelength dependence. The larger particles may represent other aerosol components or may indicate that some components, such as black carbon, have formed larger aggregates or are associated with other materials. Very small particles have a scattering wavelength dependence of $\lambda^{-4}$.

Absorption data provides information about the content of a sample besides black carbon. For example, it is known that black carbon can be coated with a variety of substances, such as organic compounds, water, and ammonium sulfate. Coatings on the particles may change their absorbance, such as by producing a lens-type effect. Details on particle coatings and their effect on absorption can be found in the following references, each of which is hereby expressly incorporated by reference in its entirety: Saathoff et al. (2003); "The AIDA soot aerosol characterization campaign 1999," *Journal of Aerosol Science* 34: 1277-1296; Schnaiter et al. (2003); "UV-VIS-NIR spectral optical properties of soot and soot-containing aerosols," *Journal of Aerosol Science* 34: 1421-1444; Gangl et al. (2004); "Increase of light absorption of carbon particles by a transparent coating: experimental evidence," *Journal of aerosol science* 35(SUPP/1): 439-440.

In particular, measuring the absorbance at multiple wavelengths may provide insight into the amount and nature of such coatings or materials. In addition, appropriate wavelength selection may allow for trace gases to be detected when aerosols are filtered out.

Figure 7:
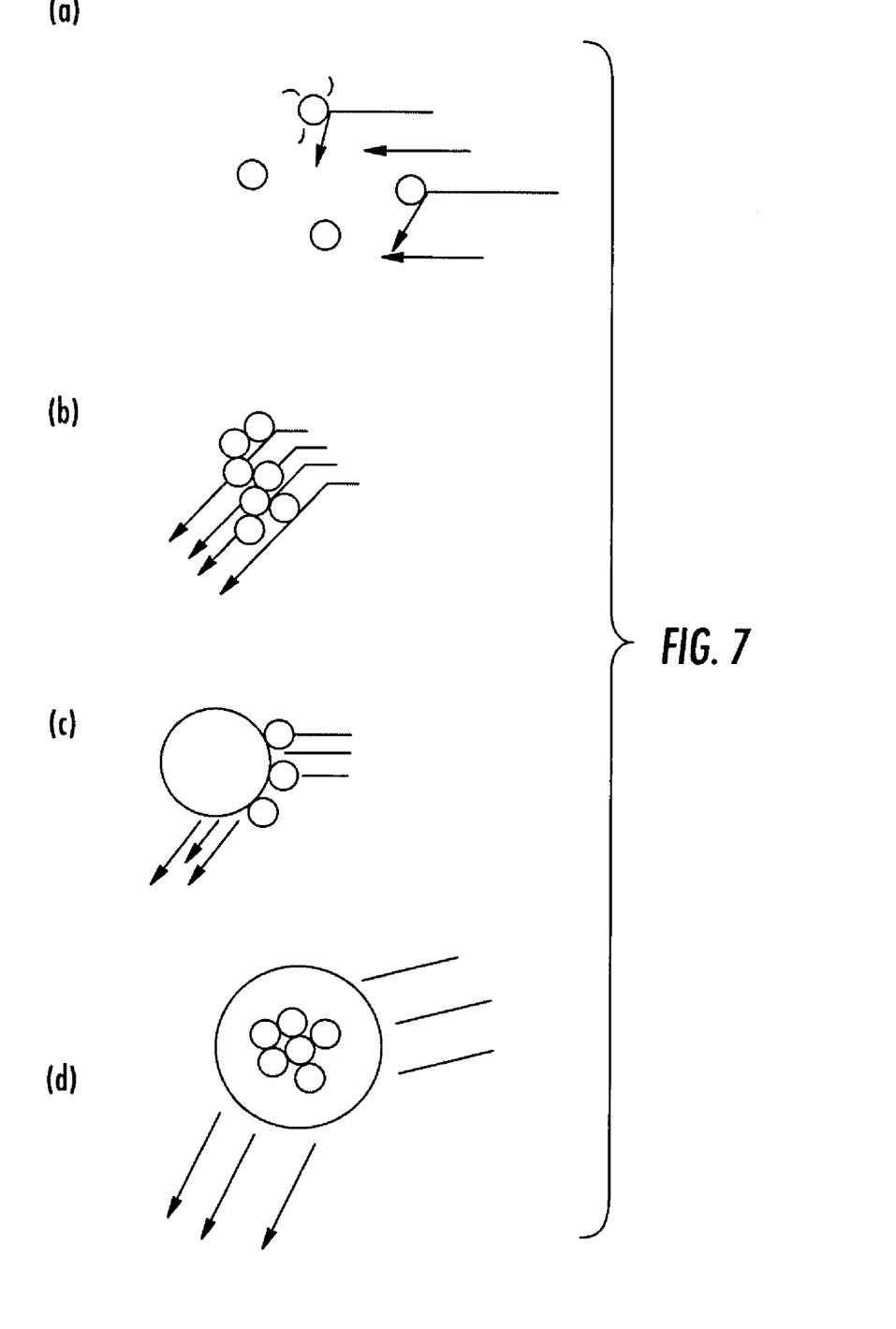
FIG. 7 is a schematic illustration of the influence of particle size and coatings on the absorption and scattering of light.

FIG. 7 presents an illustration of how the size or composition of aerosol components may affect absorption or scattering measurements. FIG. 7(a) illustrates the interaction of electromagnetic energy, such as from a laser beam, with discrete particles in an aerosol sample. As previously discussed, the particles will both scatter some of the incident radiation, which can be detected by a scattering detector, and will absorb some of the incident energy. The absorbed energy causes the particles to generate heat, which is absorbed by the surrounding air, and which generates an acoustic signal that may be measured by an acoustic detector. An optical power detector provides information about the amount of energy absorbed by the particles. The data from the acoustic detector and the optical power detector provides information on the amount of particles in the sample.

FIG. 7(*b*) illustrates the agglomeration, or coagulation, of individual particles into larger particles. The larger particle will scatter more light than the individual particles. Hence, scattering information contains information relating to particle size.

FIG. 7(*c*) illustrates coagulation between particles and other aerosol components. For example, black carbon particles may coagulate with dry sulphate particles. Again, the larger composite particle may scatter more light than discrete particles.

FIG. 7(*d*) illustrates particles, such as black carbon particles, which have been coated with a substance, such as an organic compound, water, or sulphate. Coatings may give rise to a number of effects. First, coating may increase the overall size of the particles in the aerosol. However, the coatings may also break down aggregates of particulate matter. For example, soot is known to form aggregates. These aggregates may be collapsed when they interact with coating substances. The coating may also have an effect on absorption, such as by creating a "lens" effect, which may increase the measured absorption.

Simultaneous measurement of absorption and scattering may result in faster or more accurate calibration of a photoacoustic instrument. For example, scattering calibration can be confirmed by operating the instrument with a white calibration aerosol that scatters light strongly but absorbs light negligibly, such as ammonium sulfate aerosol, or with gases such as $CO_2$ and refrigerant gases such as SUVA, which have known scattering coefficients. Under such conditions, scattering and extinction should be equal. Similarly, absorption calibration can be confirmed by operating the instrument with a black calibration aerosol that absorbs light strongly, but scatters light negligibly, such as $NO_2$. Under such conditions, absorption and extinction should be equal. Mixed white and black aerosols can then be used to evaluate instrument calibration by again measuring extinction and summing absorption and scattering to obtain the same quantity.

Current filter-based methods for aerosol light absorption do not typically allow for such closure measurements to be obtained with a single instrument. Current methods for calibration evaluation usually require the use of three separate instruments for extinction, scattering, and absorption, each with different sampling characteristics and time constants. Furthermore, the uncertainties in extinction and scattering associated with the forward scattering lobe of particles of different size and composition can easily be calculated when the photoacoustic instrument has a regular geometry, such as the instruments 200, 400 shown in FIGS. 2, 3, and 6.

Simultaneous measurements of absorption and scattering may be particularly useful in applications where the aerosol sample changes rapidly with time. For example, a photoacoustic instrument could be placed on an aircraft and used to detect and measure the properties of plumes, such as from fires or other sources. Because of the speed of the aircraft, and particularly if a plume is small or not well defined, sequential measurements may produce large errors. These errors may be reduced using certain disclosed photoacoustic instruments and methods. In addition, disclosed instruments and methods which operate at multiple wavelengths allow for more accurate insight into the composition of the plume.

Further, the wide dynamic range, small size, and sensitivity of certain disclosed photoacoustic instruments allow for convenient transport and rapid deployment of the instrument in either ground based or airborne research programs.

Multiple wavelength measurements of both scattering and absorption may also provide a fingerprint of the pollution sources and thus certain disclosed instruments can be used to help identify sources of pollution. For example, the ratio of red to blue absorption coefficient is sensitive to whether the source of organic and black carbon is from biomass burning or vehicular combustion. The ratio of red to blue light scattering is proportional to the ratio of small to large particle concentration; the angstrom coefficient derived from the multiple-wavelength scattering coefficient indicates the characteristic particle size of the size distribution. This factor can indicate particle growth and/or new particle formation.

Combustion research may utilize a fast response, wide dynamic range sensor that can profile the emissions from a wide variety of combustion sources, such as oil burners, internal combustion engines operating both on diesel and gasoline fuels, and aircraft engines. One difficulty in making such measurements is the very high concentrations of black carbon at the immediate exit of the combustion sources, which usually requiring sophisticated dilution systems. The dilution is a source of measurement uncertainty since it introduces effects that are not related to the actual combustion process. Another difficulty is designing an instrument capable of measuring over the wide range of concentrations from the center of an emission plume to its edges. The excellent dynamic range, as well as relatively fast response, of certain disclosed photoacoustic instruments makes them well suited for use in this type of research.

The disclosure is illustrated by the following non-limiting Example.

Example 1

Computer Modeling of a Photoacoustic Instrument Operating at Three Wavelengths The photoacoustic technique is typically implemented by illuminating a volume of aerosol laden air with light at a single wavelength that is modulated at the resonant frequency of the sample cavity where the air passes. Particles that absorb light at this wavelength are heated and thus heat the surrounding air, increasing the pressure inside the cavity. A sensor records this oscillating pressure, which has the frequency of the modulation of incident light and intensity proportional to the absorption coefficient of the particles. Multiple wavelengths of light may be simultaneously monitored by modulating each wavelength of light at a different frequency.

Computer model studies were conducted to examine the feasibility of operating a photoacoustic instrument with three wavelengths, with all three wavelengths operating simultaneously, but at slightly different frequencies within the passband of the acoustic resonator. The model was run using LabView software, and operating at a center frequency of 1500 Hz. The upper and lower frequencies were set at 1495 and 1505 Hz.

Figure 8:
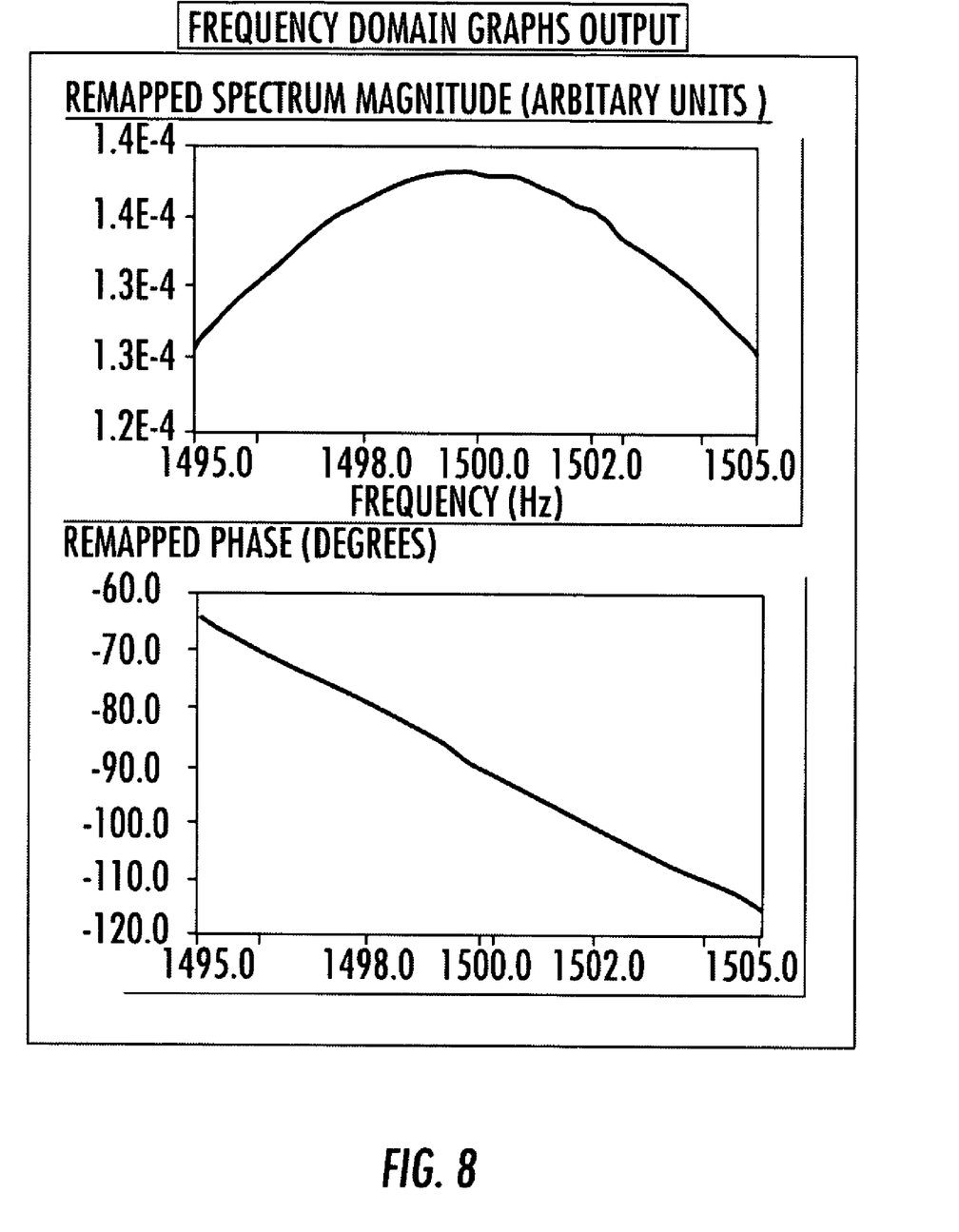
FIG. 8 is two charts illustrating a simulated acoustic resonator response for a photoacoustic instrument operating at multiple frequencies.

FIG. 8 shows the frequency domain output for this simulation over the range of 1495-1505 Hz. Operation off resonance at 1495 and 1505 Hz only results in a 10% loss in signal. The phase shift between the frequencies is linear. This data demonstrates that a three wavelength instrument may be designed with modulation at frequencies of 1495, 1500 and 1505 Hz. Data acquisition should include three channel sampling at each of the three frequencies in order to analyze the absorption coefficients at the three wavelengths. Suitable data acquisition cards with sufficient capability are available from National Instruments, such as model number 6143.

Thus, it can be seen that the present disclosure provides photoacoustic instruments and methods for their use. Certain disclosed embodiments provide photoacoustic instruments which can simultaneously measure both scattering and absorption, which may allow for more rapid or accurate calculation of extinction. Further disclosed embodiments provide photoacoustic instruments capable of simultaneously measuring absorbance, and optionally scattering, at multiple wavelengths.

It is to be understood that the foregoing is a detailed description of preferred and other embodiments. The scope of the present invention is not to be limited thereby and is to be measured by the claims, which shall embrace appropriate equivalents.

We claim:

1. A photoacoustic instrument comprising:
(A) a resonator cavity having a passband whereby the resonator cavity selectively amplifies frequencies within the passband of the resonator cavity;
(B) a plurality of lasers simultaneously optically coupleable to the resonator cavity, each of the plurality of lasers being configurable to produce a laser beam, each laser beam of the plurality of lasers having a different wavelength;
(C) a waveform generator electrically coupled to the plurality of lasers and configured to modulate the frequency of each of the laser beams within the passband of the resonator cavity;
(D) an optical power detector; and
(E) an acoustic, air-pressure detector acoustically coupled to the resonator cavity, wherein the acoustic, air-pressure detector is configured to measure the acoustic pressure of an aerosol sample;
wherein the resonator cavity is configured to receive radiation corresponding to each of the plurality of laser beams and the optical power detector is configured to detect energy corresponding to the plurality of laser beams after the plurality of laser beams have passed through the resonator cavity.

2. The photoacoustic instrument of claim 1, wherein the waveform generator modulates each of the plurality of laser beams at a different frequency within the passband of the resonator cavity, whereby the modulation allows simultaneous detection at each of the wavelengths.

3. The photoacoustic instrument of claim 1, further comprising a laser coupler, the laser coupler configured to couple the output of the plurality of lasers laser beams into a collimated beam.

4. The photoacoustic instrument of claim 3, wherein the laser coupler comprises a first fiber for receiving a first laser beam of the plurality of laser beams, a second fiber for receiving a second laser beam of the plurality of laser beams, and a collimation fiber coupled to the first and second fibers.

5. The photoacoustic instrument of claim 3, wherein the laser coupler comprises a first fiber for receiving a first laser beam produced by one of the plurality of lasers, a second fiber for receiving a second laser beam produced by another one of the plurality of lasers, a mixing chamber for combining the first and second laser beams into a collimation laser beam, and a collimation fiber for receiving the collimation laser beam.

6. The photoacoustic instrument of claim 5, wherein the mixing chamber comprises a dichroic mirror in communication with the first and second fibers.

7. The photoacoustic instrument of claim 1, further comprising a scattering detector in communication with the resonator cavity.

8. The photoacoustic instrument of claim 7, wherein the scattering detector is a multiwavelength scattering detector configured to at least substantially simultaneously measure scattering at the plurality of wavelengths.

9. The photoacoustic instrument of claim 1, wherein the output of the plurality of lasers is configured to pass through the resonator cavity at least substantially simultaneously.

10. A photoacoustic measurement method comprising:
generating a plurality of laser beams, each of the laser beams having a different wavelength or wavelength band, each wavelength band comprising a plurality of wavelengths, each wavelength having an energy;
modulating the frequencies of the plurality of laser beams within the passband of an acoustic resonator, whereby the acoustic resonator selectively amplifies frequencies within the passband of the acoustic resonator;
at least substantially simultaneously irradiating a sample with the plurality of laser beams;
detecting sound produced by interacting the sample with the radiation simultaneously at each of the plurality of wavelengths or wavelength bands; and
detecting energy absorbed by the sample at each of the plurality of wavelengths or wavelength bands.

11. The photoacoustic measurement method of claim 10, wherein irradiating the sample with radiation having a plurality of wavelengths or wavelength bands comprises irradiating the sample with a laser beam comprising the plurality of wavelengths or wavelength bands.

12. The photoacoustic measurement method of claim 10, wherein irradiating the sample with radiation having a plurality of wavelengths or wavelength bands comprises irradiating the sample with a plurality of laser beams.

13. The photoacoustic measurement method of claim 10, further comprising detecting scattered energy produced by the sample interacting with the radiation.

14. The photoacoustic measurement method of claim 10, further comprising, at each of the plurality of wavelengths or wavelength bands, detecting scattered energy produced from the sample interacting with the radiation.

15. The photoacoustic measurement method of claim 10, wherein irradiating the sample with radiation having a plurality of wavelengths or wavelength bands comprises passing the radiation multiple times through a sample chamber.

* * * * *